(12) United States Patent
Bergmann et al.

(10) Patent No.: US 9,829,494 B2
(45) Date of Patent: Nov. 28, 2017

(54) METHODS OF TREATMENT USING ADM ANTIBODIES

(75) Inventors: Andreas Bergmann, Berlin (DE); Joachim Struck, Berlin (DE); Nils G. Morgenthaler, Berlin (DE)

(73) Assignee: ADRENOMED AG, Hennigsdorf (DE)

( * ) Notice: Subject to any disclaimer, the term of this patent is extended or adjusted under 35 U.S.C. 154(b) by 697 days.

(21) Appl. No.: 12/095,675

(22) PCT Filed: Dec. 1, 2005

(86) PCT No.: PCT/EP2005/012844
§ 371 (c)(1),
(2), (4) Date: May 30, 2008

(87) PCT Pub. No.: WO2007/062676
PCT Pub. Date: Jun. 7, 2007

(65) Prior Publication Data
US 2010/0209433 A1 Aug. 19, 2010

(51) Int. Cl.
*G01N 33/53* (2006.01)
*A61K 39/395* (2006.01)
*G01N 33/74* (2006.01)
*C07K 16/26* (2006.01)

(52) U.S. Cl.
CPC .......... *G01N 33/74* (2013.01); *A61K 39/3955* (2013.01); *C07K 16/26* (2013.01)

(58) Field of Classification Search
None
See application file for complete search history.

(56) References Cited

U.S. PATENT DOCUMENTS

| | | | |
|---|---|---|---|
| 5,427,908 A | 6/1995 | Dower et al. | |
| 5,580,717 A | 12/1996 | Dower et al. | |
| 5,585,089 A | 12/1996 | Queen et al. | |
| 5,639,855 A | 6/1997 | Kitamura et al. | |
| 5,807,715 A | 9/1998 | Morrison et al. | |
| 5,830,703 A | 11/1998 | Kitamura et al. | |
| 5,837,823 A * | 11/1998 | Kitamura et al. | 530/387.9 |
| 5,910,416 A | 6/1999 | Kitamura et al. | |
| 5,939,598 A | 8/1999 | Kucherlapati et al. | |
| 5,969,108 A | 10/1999 | McCafferty et al. | |
| 6,114,598 A | 9/2000 | Kucherlapati et al. | |
| 6,197,069 B1 * | 3/2001 | Poste et al. | 435/69.1 |
| 6,756,483 B1 * | 6/2004 | Bergmann et al. | 530/399 |
| 6,818,418 B1 | 11/2004 | Lipovsek et al. | |
| 6,864,237 B2 * | 3/2005 | Wang | 514/2.4 |
| 6,884,781 B2 | 4/2005 | Wang et al. | |
| 7,064,107 B2 | 6/2006 | Ladner et al. | |
| 7,361,473 B2 | 4/2008 | Valkirs et al. | |
| 7,622,272 B2 | 11/2009 | Cuttitta et al. | |
| 7,635,666 B1 | 12/2009 | McCafferty et al. | |
| 7,659,081 B2 * | 2/2010 | Cuttitta et al. | 435/7.1 |
| 7,723,270 B1 | 5/2010 | McCafferty et al. | |
| 7,811,991 B2 | 10/2010 | Ladner et al. | |
| 7,851,442 B2 | 12/2010 | Ladner et al. | |
| 8,124,586 B2 | 2/2012 | Ladner et al. | |
| 8,278,262 B2 | 10/2012 | Kolmar et al. | |
| 8,710,007 B2 | 4/2014 | Ladner et al. | |
| 8,732,649 B2 | 5/2014 | Hartl | |
| 2002/0055615 A1 * | 5/2002 | Cuttitta et al. | 530/300 |
| 2004/0023334 A1 | 2/2004 | Prior | |
| 2004/0038893 A1 | 2/2004 | Ladner et al. | |
| 2005/0076395 A1 | 4/2005 | Kucherlapati et al. | |
| 2005/0164301 A1 | 7/2005 | Kolkman et al. | |
| 2005/0255548 A1 | 11/2005 | Lipovsek et al. | |
| 2006/0194727 A1 | 8/2006 | Ladner et al. | |
| 2007/0082363 A1 | 4/2007 | Bougueleret et al. | |
| 2007/0212742 A1 * | 9/2007 | Bergmann et al. | 435/7.93 |
| 2007/0280886 A1 | 12/2007 | Golz et al. | |
| 2008/0064637 A1 | 3/2008 | Ladner et al. | |
| 2008/0076717 A1 | 3/2008 | Rowe | |
| 2008/0131426 A1 | 6/2008 | Ladner et al. | |

(Continued)

FOREIGN PATENT DOCUMENTS

EP 0353971 A2 2/1990
EP 0622458 A2 11/1994

(Continued)

OTHER PUBLICATIONS

Richards, A. M., et al., "Plasma N-Terminal Pro-Brain Natriuretic Peptide and Adrenomedullin: New Neurohormonal Predictors of Left Ventricular Function and Prognosis After Myocardial Infarction," Circulation—Journal of the American Heart Association, 1998; 97; 1921-1929—Downloaded from circ.ahajournals.org on Jan. 19, 2010.

Qi, Y. F., et al., "Effects of Different Peptide Fragments Derived from Proadrenomedullin on Gene Expression of Adrenomedullin Gene," Peptides 23 (2002) 1141-1147.

Hyvelin et al. "Adrenomedullin: a cardiac depressant factor in septic shock." J Card Surg., 17(4):328-35, 2002.

Ouafik et al., "Neutralization of adrenomedullin inhibits the growth of human glioblastoma cell lines in vitro and suppresses tumor xenograft growth in vivo," Am J Pathol., 160(4):1279-92, 2002.

Champion et al., "Structure-activity relationships of adrenomedullin in the circulation and adrenal gland," Regul Pept., 30;85(1):1-8, 1999.

(Continued)

Primary Examiner — Marianne P Allen
(74) Attorney, Agent, or Firm — Millen, White, Zelano, Branigan, P.C.

(57) ABSTRACT

The ratio of concentrations of pro-adrenomedullin (pro-ADM)/pro-endothelin (pro-END) immunoreactivity in body fluids of critically ill patients is used as for the diagnosis, course control and prognosis, including an assessment of the mortality risk, of severe life threatening diseases. Further, a treatment of critically ill patients having high levels of pro-ADM but insufficient levels of pro-END immunoreactivities with a medicament comprising vasoconstrictive endothelin or its precursors, and/or endothelin agonists or adrenomedullin antagonists is provided.

5 Claims, 4 Drawing Sheets

(56) References Cited

U.S. PATENT DOCUMENTS

| | | | |
|---|---|---|---|
| 2008/0152656 | A1 | 6/2008 | Ladner et al. |
| 2008/0200646 | A1 | 8/2008 | Ladner et al. |
| 2008/0260752 | A1 | 10/2008 | Ladner et al. |
| 2009/0082267 | A1 | 3/2009 | Ladner et al. |
| 2009/0130692 | A1 | 5/2009 | Kolmar et al. |
| 2010/0028995 | A1 | 2/2010 | Graversen et al. |
| 2010/0209433 | A1 | 8/2010 | Bergmann et al. |
| 2010/0317540 | A1 | 12/2010 | McCafferty et al. |
| 2011/0086801 | A1 | 4/2011 | Ladner et al. |
| 2011/0207668 | A1 | 8/2011 | Binz et al. |
| 2012/0129710 | A1 | 5/2012 | McCafferty et al. |
| 2013/0005659 | A1 | 1/2013 | Grabulovski et al. |
| 2013/0061104 | A1 | 3/2013 | Hartl |
| 2013/0085113 | A1 | 4/2013 | Hohlbaum et al. |
| 2013/0315912 | A1 | 11/2013 | Mabrouk et al. |

FOREIGN PATENT DOCUMENTS

| | | | |
|---|---|---|---|
| EP | 1266025 | B1 | 12/2002 |
| EP | 1 488 209 | B1 * | 1/2004 |
| EP | 1941867 | A1 | 7/2008 |
| EP | 2314308 | A1 | 4/2011 |
| EP | 2231860 | B1 | 10/2011 |
| WO | 9110741 | A1 | 7/1991 |
| WO | 9117271 | A1 | 11/1991 |
| WO | 9201047 | A1 | 1/1992 |
| WO | 9220791 | A1 | 11/1992 |
| WO | 9312227 | A1 | 6/1993 |
| WO | 2004090546 | A1 | 10/2004 |
| WO | WO 2004/090546 | * | 10/2004 |
| WO | 2004097423 | A1 | 11/2004 |
| WO | 2005040229 | A2 | 5/2005 |
| WO | 2006027147 | A2 | 3/2006 |
| WO | 2007062676 | A1 | 6/2007 |
| WO | 2010060748 | A1 | 6/2010 |
| WO | 2011023685 | A1 | 3/2011 |
| WO | 2011107321 | A1 | 9/2011 |
| WO | 2011154420 | A2 | 12/2011 |

OTHER PUBLICATIONS

Mazzocchi et al., "Adrenomedullin (ADM), acting through ADM(22-52)-sensitive receptors, is involved in the endotoxin-induced hypotension in rats," Life Sci., 3;66(15):1445-50, 2000.

Wang et al., "The Pivotal Role of Adrenomedullin in Producing Hyperdynamic Circulation During the Early Stage of Sepsis," Arch Surg., 1998;133:1298-1304.

Hasback et al. "CGRP receptors mediating CGRP-, adrenomedullin- andamylin-induced relaxation in porcine coronary arteries. Characterization with 'Compound 1' (WO98/11128), anon-peptide antagonist." British Journal of Pharmacology, 133, 1405-1413, 2001.

Wagner, K., et al., "Adrenomedullin blockade improves catecholamine responsiveness and kidney function in resuscitated murine septic shock," Category 1: Sepsis—basic mechanisms—mediators—immunology; Category 2: Sepsis. Poster, 32$^{nd}$ Inter. Symp. On INt. Care and Emerg. Med., Brussels, BE, Mar. 20-23, 2012.

Meeran, K., et al., "Circulating Adrenomedullin Does Not Regulate Systemic Blood Pressure but Increases Plasma Prolactin after Intravenous Infusion in Humans: A Pharmacokinetic Study," Journal of Clinical Endocrinology and Metabolism, vol. 82, No. 1, pp. 95-100, 1997.

Ohta, H., et al., "One-Step Direct Assay for Mature-type Adrenomedullin with Monoclonal Antibodies," Clinical Chemistry, Endocrinology and Metabolism, 45:2, 244-251 (1999).

Webster, N.R., "Monitoring the critically ill patient," Educational Review, J.R. Coll. Surg. Edinb., 44, Dec. 1999, 386-93.

"Care of the Critically Ill Adult," Am. Ac. Of Family Physicians, AAFP Reprint No. 291, pp. 1-10, published Jun. 2003.

Takashi Kondoh et al. "Pre-treatment of adrenomedullin suppresses cerebral edema caused by transient focal cerebral ischemia in rats detected by magnetic resonance imaging" Brain Research Bulletin [2011], vol. 84, No. 1, pp. 69-74.

Struck, J. et al., "Method for the selective measurement of amino-terminal variants of procalcitonin," Clinical Chemistry, 2009, vol. 55, No. 9, pp. 1672-1679.

Meissner et al., "Safety and Phamacokinetics of an Intramuscular Monoclonal Antibody (SB 209763) against Respiratory Syncytial Virus (RSV) in Infants and Young Children at Risk for Severe RSV Disease," Antimicrob Agents Chemother, 1999, vol. 43, pp. 1183.

Meghan M. Taylor et al. "Ribozyme compromise of adrenomedullin mRNA reveals a physiological role in the regulation of water intake" American Journal of Physiology, [2002], vol. 282, No. 6, pp. R1739-R1745.

Willis K. Samson et al. "Adrenomedullin Inhibits Salt Appetite" [1997], vol. 138, No. 2, pp. 613-616.

Willis K. Samson "Adrenomedullin and the control of fluid and electrolyte homeostasis" Annual Review of Physiology, [1999], vol. 61, No. 1, pp. 363-389.

A. Martinez et al. "Is Adrenomedullin a Causal Agent in Some Cases of Type 2 Diabetes?" Peptides, [1999], vol. No. 12, pp. 1471-1478.

Meghan M. Taylor et al. "Adrenomedullin and the Integrative Physiology of Fluid and Electrolyte Balance" Microscopy Research and Technique, [2002], vol. 57, No. 2, pp. 105-109.

Duc Quyen Chu et al. "The calcitonin gene-related peptide (CGRP) antagonist CGRP 8-37 blocks vasodilatation ininflamed rat skin: involvement of adrenomedullin in addition to CGRP" Neuroscience Letter, [2001], vol. 310, No. 2-3, pp. 169-172.

Albuszies G et al.: 'Effect of increased cardiac output on hepatic and intestinal microcirculatory blood flow, oxygenation, and metabolism in hyperdynamic murine septic shock' Crit Care Med vol. 33, 2005, pp. 2332-2338.

Albuszies G et al.: 'The effect of iNOS deletion on hepatic gluconeogenesis in hyperdynamic murine septic shock' Intensive Care Med vol. 33, 2007, pp. 1094-1101.

Almagro JC; Fransson J.: 'Humanization of antibodies' Front Biosci. vol. 13, Jan. 1, 2008, pp. 1FI19-1FI33.

Barth—Role of inducible nitric oxide synthase in the reduced responsiveness of the myocardium to catecholamines in a hyperdynamic murine model , Crit Care Med. Feb. 2006;34(2):307-13.

Baumgart K et al.: 'Effect of SOD-1 over-expression on myocardial function during resuscitated murine septic shock' Intensive Care Med vol. 35, 2009, pp. 344-349.

Beale, D: 'Molecular fragmentation: Some applications in immunology' Exp Comp Immunol vol. 11, 1987, pp. 287-296.

Bird et al. 'Single-Chain Antigen-Binding Proteins' Science vol. 242, 1988, pp. 423-426.

Chen X. et al.: 'Requirement of open headpiece conformation for activation of leukocyte integrin axp2' PNAS vol. 107, 2010, pp. 14727-14732.

Chintala MS; Bernardino V; Chiu PJS: 'Cyclic GMP but not cyclic AMP prevents renal platelet accumulation following ischemiareperfusion in anesthetized rats' J Pharmacolexpther vol. 271, 1994, pp. 1203-1208.

Chiu PJS: 'Models used to assess renal functions' Drug Develop Res vol. 32, 1994, pp. 247-255.

Chu et al., Neuroscience letters, 2001, vol. 301, No. 2-3, pp. 169-172.

Coulter, A.; Harris, R. J. Simplified preparation of rabbit Fab fragments , Immunol. Meth. vol. 59, 1983, pp. 199-203.

Ehlenz, K. et al.: 'High levels of circulating adrenomedullin in severe illness: Correlation with C-reactive protein and evidence against the adrenal medulla as site of origin' Exp Olin Endocrinol Diabetes vol. 105, 1997, pp. 156-162.

Ellerson, J.R. et al.: 'A fragment corresponding to the CH2 region of immunoglobulin G (IgG) with complement fixing activity' FEBS Letters vol. 24, No. 3, 1972, pp. 318-322.

(56) References Cited

OTHER PUBLICATIONS

Eto, T.: 'A review of the biological properties and clinical implications of adrenomedullin and proadrenomedullin N-terminal 20 peptide (PAMP), hypotensive and vasodilating peptides' Peptides vol. 22, 2001, pp. 1693-1711.

Gebauer M et al: "Engineered protein scaffolds as next-generation antibody therapeutics", Current Opinion in Chemical Biology, Current Biology Ltd, London, GB, vol. 13, No. 3, Jun. 1, 2009 (Jun. 1, 2009), pp. 245-255, XP026285197, ISSN: 1367-5931, DOI: 10.1016/J.CBPA.2009.04.627 [retrieved on Jun. 6, 2009].

Harris, L; Bajorath, J: 'Profiles for the analysis of immunoglobulin sequences: Comparison of V gene subgroups' Protein Sci. vol. 4, 1995, pp. 306-310.

Hunkapiller; Hood 'The growing Immunoglobulin gene superfamily', Nature vol. 323, 1986, pp. 15-16.

Huston et al. 'Protein engineering of antibody binding sites: Recovery of specific activity in an anti-digoxin single-chain Fv analogue produced in *Escherichia coli*' Proc. Natl. Acad. Sci. U.S.A. vol. 85, 1988, pp. 5879-5883.

Hust, M.; Meyer, T.; Voedisch, B.; Rulker, T.; Thie, H.; El-Ghezal, A.; Kirsch, M.I.; Schütte, M.; Helmsing, S.; Meier, D.: 'A human scFv antibody generation pipeline for proteome research' Journal of Biotechnology vol. 152, 2011, pp. 159-170.

Hyvelin J et al: "Adrenomedullin: A Cardiac Depressant Factor in Septic Shock", Journal of Cardiac Surgery, Futura Publ., Mount Kisco, NY, US, vol. 17, No. 4, Jan. 1, 2002 (Jan. 1, 2002), pp. 328-335, XP007915796, ISSN: 0886-0440 [retrieved on Jul. 12, 2010].

Jacob: 'Acute Renal Failure' Indian J. Anaesth. vol. 47, No. 5, 2003, pp. 367-372.

Jones, P. T.; Dear, P. H.; Foote, J.; Neuberger, M. S.; Winter, G.: 'Replacing the complementarity-determining regions in a human antibody with those from a mouse' Nature vol. 321, 1986, pp. 522-525.

Kaufmann B. et al.: 'Neutralization of West Nile virus by cross-linking of its surface proteins with Fab fragments of the human monoclonal antibody CR4354' PNAS vol. 107, 2010, pp. 18950-18955.

Kerbel, R.S.; Elliot, B.E.: 'Detection ofFc receptors' Meth Enzymol vol. 93, 1983, pp. 113-147.

Kong F. et al.: 'Demonstration of catch bonds between an integrin and its ligand' J. Cell Biol. vol. 185, 2009, pp. 1275-1284.

Kulkarni, P.N. et al.: 'Conjugation of methotrexate to IgG antibodies and their F(ab')2 fragments and the effect of conjugated methotrexate on tumor growth in vivo' Cancer Immunol Immunotherapy vol. 19, 1985, pp. 211-214.

Kuwasako et al, Purification and characterization of PAMP-12 (PAMP-20) in porcine adrenal medulla as a major endogenous biologically active peptide ; FEBS Lett. Sep. 1, 1997;414(1):105-10.

Kuwasako, K. et al.: 'Increased plasma proadrenomedullin N-terminal 20 peptide in patients with essential hypertension' Ann. Clin. Biochem. vol. 36, 1999, pp. 622-628.

Lamoyi, E.: 'Preparation of F(ab')2 Fragments from mouse IgG of various subclasses' Meth Enzymol vol. 121, 1986, pp. 652-663.

Lane, R.D.: 'A short-duration polyethylene glycol fusion technique for increasing production of monoclonal antibody-secreting hybridomas' J. Immunol. Meth. vol. 81, 1985, pp. 223-228.

Lanzavecchia et al. 'The use of hybrid hybridomas to target human cytotoxic T lymphocytes' Eur. J Immunol. vol. 17, issue 1, 1987, p. 105.

Lindner I. et al.: 'alpha)2-Macroglobulin inhibits the malignant properties of astrocytoma cells by impeding {beta}-catenin signaling' Cancer Res. vol. 70, 2010, pp. 277-287.

Lorenz et al.: 'Functional Antibodies Targeting IsaA of *Staphylococcus aureus* Augment Host Immune Response and Open New Perspectives for Antibacterial Therapy' Antimicrob Agents Chemother. vol. 55, No. 1, Jan. 2011, pp. 165-173.

Mariani, M.: 'A new enzymatic method to obtain high-yield F(ab')2 suitable for clinical use from mouse IgGI' Mol. Immunol. vol. 28, 1991, pp. 69-77.

Martinez et al., Peptides, 1999 vol. 20, No. 12.pp. 1471-1478.

Martinez et al.: 'Mapping of the Adrenomedullin-Binding domains in Human Complement factor H' Hypertens Res vol. 26, 2003, pp. 56-59.

Marx et al.: 'Monoclonal Antibody Production' ATLA vol. 25, 1997, p. 121.

Miller Mae Jean et al: "Adrenomedullin expression in human tumor cell lines: Its potential role as an autocrine growth factor", Journal of Biological Chemistry, American Society for Biochemistry and Molecular Biology, US, vol. 271, No. 38, Sep. 1, 1996 (Sep. 1, 1996), pp. 23345-23351, XP002184272, ISSN: 0021-9258, DOI: 10.1074/JBC.271.38.23345.

Nakamoto M; Shapiro JI; Shanley PF; Chan L; Schrier RW: 'In vitro and in vivo protective effect of atriopeptin III on ischemic acute renal failure' J Clinlnvest vol. 80, 1987, pp. 698-705.

Padlan, E. A.: 'A possible procedure for reducing the immunogenicity of antibody variable domains while preserving their ligand-binding properties' Mol. Immunol. vol. 28, 1991, pp. 489-498.

Parham, P. et al.: 'Monoclonal antibodies: purification, fragmentation and application to structural and functional studies of class I MHC antigens' J Immunol Meth vol. 53, 1982, pp. 133-173.

Ping Wang: "Andrenomedullin and cardiovascular responses in sepsis", Peptides, vol. 22, No. 11, Nov. 1, 2001 (Nov. 1, 2001), pp. 1835-1840, XP055022163, ISSN: 0196-9781, DOI: 10.1016/S0196-9781(01)00534-4.

Pio R et al: "Complement Factor H Is a Serum-binding Protein for Adrenomedullin, and the Resulting Complex Modulates the Bioactivities of Both Partners", Journal of Biological Chemistry, American Society for Biochemistry and Molecular Biology, US, vol. 276, No. 15, Apr. 1, 2001 (Apr. 1, 2001), pp. 12292-12300, XP009119203, ISSN: 0021-9258, DOI: 10.1074/JBC.M007822200 [retrieved on Dec. 14, 2000].

Rousseaux, J. et al.: 'The differential enzyme sensitivity of rat immunoglobulin G subclasses to papain and pepsin' Mol Immunol vol. 17, 1980, pp. 469-482.

Pio et al, Identification, characterization, and physiological actions of factor H as an Adrenomedullin binding Protein present in Human Plasma Microsc Res Tech. Apr. 1, 2002;57(1):23-7.

Quafik et al., "Neutralization of Adrenomedullin Inhibits the Growth of Human Glioblastoma Cell Lines in Vitro and Suppresses Tumor Xenograft Growth in Vivo", American Journal of Pathology, vol. 160, No. 4, 2002, pp. 1279-1292.

Raychaudhuri, G. et al.: 'Human IgGI and its Fc fragment bind with different affinities to the Fc receptors on the human U937, HL-60 and ML-1 cell lines' Mol Immunol vol. 22, No. 9, 1985, pp. 1009-1019.

Rousseaux, J. et al.: 'Optimal condition for the preparation of Fab and F(ab')2 fragments from monoclonal IgG of different rat IgG subclasses' J Immunol Meth vol. 64, 1983, pp. 141-146.

Scales and Pilsworth 'The importance of fluid balance in clinical practice' Nursing Standard vol. 22, No. 47, 2008, pp. 50-57.

Schrier; Wang: 'Mechanisms of Disease Acute Renal Failure and Sepsis' The New England Journal of Medicine vol. 351, 2004, pp. 159-169.

Schütte, M.; Thullier, P.; Pelat, T.; Wezler, X.; Rosenstock, P.; Hinz, D.; Kirsch, M.I.; Hasenberg, M.; Frank, R.; Schirrmann, T: 'Identification of a putative Crf splice variant and generation of recombinant antibodies for the specific detection of Aspergillus fumigatus' PLOS ONE vol. 4, 2009, p. E6625.

Alison Shepherd 'Measuring and managing fluid balance' Nursing Times vol. 107, No. 28, pp. 12-16 (2011).

Simkova V et al.: 'The effect of SOD-1 over-expression on hepatic gluconeogenesis and whole-body glucose oxidation during resuscitated, normotensive murine septic shock' Shock vol. 30, 2008, pp. 578-584.

Struck et al., Clin. Chem 55:9-1672-1679 (2009).

Takahashi, K.: 'Adrenomedullin: from a pheochromocytoma to the eyes', 'Peptides', vol. 22, 2001, p. 1691.

(56) References Cited

OTHER PUBLICATIONS

Thomas G. M. et al.: 'Cancer cell-derived microparticles bearing P-selectin glycoprotein ligand 1 accelerate thrombus formation in vivo' J. Exp. Med. vol. 206, 2009, pp. 1913-1927.
Tomoda, Y. et al.: 'Regulation of adrenomedullin secretion from cultured cells' Peptides vol. 22, 2001, pp. 1783-1794.
Tsuruda, T. et al.: 'Secretion of proadrenomedullin N-terminal 20 peptide from cultured neonatal rat cardiac cells' Life Sci. vol. 69, No. 2, 2001, pp. 239-245.
Uysal H. et al.: 'Structure and pathogenicity of antibodies specific for citrullinated collagen type II in experimental arthitis' J. Exp. Med. vol. 206, 2009, pp. 449-462.
Wagner F et al_2011_Inflammatory effects of hypothermia and inhaled H2S during resuscitated, hyperdynamic murine septic shock SHOCK, vol. 35, No. 4, pp. 396Y402, 2011.
Wagner F; Scheuerle A; Weber S; Stahl B; McCook O; Kn6ferl MW; Huber-Lang M; Seitz DH; Thomas J; Asfar P: 'Cardiopulmonary, histologic, and inflammatory effects of intravenous Na2S after blunt chest trauma-induced lung contusion in mice' J Trauma vol. 71, No. 6, 2011, pp. 1659-1667.
Ping Wang et al: "The Pivotal role of adrenomedullin in producing hyperdynamic circulation during early stage of sepsis", Archives of Surgery, American Medical Association, Chicago, IL, US, vol. 133, Dec. 1, 1998 (Dec. 1, 1998), pp. 1298-1304, XP002599345, ISSN: 0004-0010.
Wilson, K.M. et al.: 'Rapid whole blood assay for HIV-1 seropositivity using an Fab-peptide conjugate' J Immunol Meth vol. 138, 1991, pp. 111-119.
Wu R et al: "Human vasoactive hormone adrenomedullin and its binding protein rescue experimental animals from shock", Peptides, Elsevier, Amsterdam, NL, vol. 29, No. 7, Jul. 1, 2008 (Jul. 1, 2008), pp. 1223-1230, XP022704824, ISSN: 0196-9781, DOI: 10.1016/J. PEPTIDES.2008.02.021 [retrieved on Mar. 8, 2008].
Wurch Thierry et al: "Novel protein scaffolds as emerging therapeutic proteins: from discovery to clinical proof-of-concept", Trends in Biotechnology, vol. 30, No. 11, Nov. 2012 (Nov. 2012), pp. 575-582, ISSN: 0167-7799.
Moody, T. W. et al., "Adrenomedullin binds with affinity, elevates cyclic amp, and stimulates c-fos mRNA in C6 Glioma Cells," Peptides, 1997, vol. 18, No. 8, pp. 1111-1115.
Wurch, T. et al., "Novel Protein scaffolds as emerging therapeutic proteins: From discovery to clinical proof-of-concept," Trends in Biotechnology, Nov. 2012, vol. 30, No. 11, pp. 575-582.
Meissner et al.. "Safety and Phamacokinetics of an Intramuscular Monoclonal Antibody (SB 209763) against Respiratory Syncytial Virus (RSV) in Infants and Young Children at Risk for Severe RSV Disease," Antimicrob Agents Chemother, 1999, vol. 43, pp. 1183.
Breen et al., "Effect of moisture on the stability of a lyophilized humanized monoclonal antibody formulation," Pharm. Res., 2001, vol. 18, pp. 1345-1353.
Degoricija et al., "Survivial Analysis of 314 episodes of sepsis in medicinal intensive care unit in University Hospital: Impact of Intensive Care Unit Performance and Antimicrobial Therapy," Croatian Med. J., 2006, vol. 47, pp. 385-397.
Benito et al., "Lack of value of midregional pro-adrenomedullin and C-terminal pro-endothelin-1 for prediction of severe bacterial infections in infants with fever without a source," Eur. J. Pediatr., 2013, vol. 172, pp. 1441-1449.
Kitamura, K., et al., "The Intermediate Form of Glycine-Extended Adrenomedullin Is the Major Circulating Molecular Form in Human Plasma," Biochem. Biophys. Res. Commun., vol. 244, No. 2, 1998, pp. 551-555.
Hirata, Y., et al., "Increased Circulating Adrenomedullin, a Novel Vasodilatory Peptide, in Sepsis," Jrnl. of Clin. Endo. Metab., vol. 81, No. 4, 1996, pp. 1449-1453.
Schuetz. P., et al., "Circulating Precursor Levels of Endothelin-1 and Adrenomedullin, Two Endothelium-Derived, Counteracting Substances, in Sepsis," Endothelium, vol. 14, 2007, pp. 345-351.
Nishio, K., M.D., et al., "Increased plasma concentrations of adrenomedullin correlate with relaxation of vascular tone patients with septic shock," Crit. Care Med., vol. 25, No. 6, 1997, pp. 953-957.
Hinson et al., "Adrenomedullin, a Multifunctional Regulatory Peptide", Endocrine Reviews, vol. 21, No. 2, 2000, pp. 138-167.
Ueda et al., "Increased Plasma Levels of Adrenomedullin in Patients with Systemic Inflammatory Response Syndrome", Am. J. Respir. Cult. Care Med., vol. 160, 1999, pp. 132-136.

* cited by examiner

METHODS OF TREATMENT USING ADM ANTIBODIES

CROSS REFERENCE TO RELATED APPLICATIONS

This application is a 371 filing of PCT International application no. PCT/EP2005/012844 filed Dec. 1, 2005 and published as WO 2007/062676 on Jun. 7, 2007; the disclosure of this application and all other patents, published applications and other references cited herein are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Sep. 9, 2010, is named BOEH0050.txt and is 7,023 bytes in size.

The present invention relates to novel diagnostic, and derived therapeutic, methods useful for the diagnosis and treatment of a group of severe, life threatening diseases. The invention can also be considered as relating to the field of intensive care medicine.

More specially, the invention is based on the surprising finding that the physiological release of two different vasoactive types of peptides, namely of peptides of the adrenomedullin and endothelin families, for which it was already reported that they can be found elevated during potentially life threatening conditions as e.g. sepsis and other severe conditions, if considered in combination, provides new and highly relevant information on the actual status of a critically ill patient and his prognosis. A detected imbalance of the peptides of said families, at least if determined by means of suitable methods providing information on the release of said peptides rather than on their actual level in a body fluid, above certain critical threshold concentration levels in the circulation of the patient, enables a physician to intervene and to restore said balance so that the patient gets a chance to recover from an acute crisis which otherwise would lead to his death.

The diseases for which the invention is contemplated as being of high diagnostic and therapeutic value comprise sepsis, SIRS, septic shock, MOF (multiple organ failure), severe systemic or local infections, especially bacterial infections, peritonitis, pancreatitis, local and/or systemic inflammation, meningitis, trauma, ruptured aortic aneurysm, intoxication, endotoxemia, anuria, renal insufficiency, arterial hypertension, pulmonary hypertension, artherosclerosis, several types of cancer, for example colorectal cancer, congestive heart failure, cardiovascular diseases, coronary artery disease, ischemia, antiarrhythmic effects, renal and/or heart failure, organ injury, and diseases related to growth, and others.

The invention is based on the surprising finding that high levels of vasoactive peptides of the endothelin family, which can be determined by measuring peptides indicating a high physiological release of the potent vasoconstrictors as endothelin-1, in critically ill patients with high levels of adrenomedullin can exert a beneficial, potentially life saving effect. In the scientific literature, in which occasionally speculations about an antagonistic behaviour of adrenomedullin and endothelin peptides can be found, high concentrations of the vasoconstrictors of the endothelin family are constantly considered as dangerous and undesirable. High levels of adrenomedullin, on the contrary, are regarded as positive. An example for such speculations is found in the publication of Takayuki Shindo et al., Hypotension and Resistance to Lipopolysaccharide-Induced Shock in Transgenic Mice Overexpressing Adrenomedullin in Their Vasculature, In: Circulation. 2000; 101:2309-2316.

The applicants have determined the formation or release of peptides of the adrenomedullin and endothelin families in critically ill patients, using new assays measuring prohormone (propeptide) immunoreactivities which provide information on the physiological release of both types of peptides rather than on the actual levels of the "mature" peptides in the circulation, and they found that under certain circumstances explained in more detail below in the examples in connection with the results of measurements of sera of critically ill patients, a dramatic decrease of measurable endothelin formation, while at the same time the levels of released adrenomedullin are critically high, precedes the death of such patients.

Based on said findings the applicants have defined a condition called "low endothelin syndrome" (in the following briefly LES) or "endothelin deficiency syndrome" which is characterized by a life threatening change in the release phase of endothelin (more specially of "endothelin-r" or "END-r" as it is defined below) in relation to the release of adrenomedullin (more specially "adrenomedullin-r" or "ADM-r" as it is defined below). Said syndrome is characterized by a high systemic concentration, or a high release rate, of the vasodilator adrenomedullin and, concomitantly, by an insufficient release rate of the vasoconstrictor endothelin (END-r). The consequence of such mismatch is an uncontrollable vasodilation and an insufficient supply of one or more organs with blood, i.e. a single or multiple organ failure.

In the present application the suffix "-r", used in terms as END-r or ADM-r, stands for "released". It means that the parameter in question is not the actual, more or less momentary or transient measurable serum or plasma concentration of the biologically active biomolecule (mature peptide) in question but rather reflects its cumulative release over a longer period of time. It can be directly measured e.g. by measuring a peptide fragment formed from the physiological precursor peptide (pre-pro- or pro-peptide or -hormone) concomitantly with the formation of the active biomolecule, which fragment, however, has a considerably longer half life in the circulation (a considerably slower degradation or clearance rate) than the active biomolecule. Assays for measuring ADM-r are described in applicants' European patent EP 1 488 209 B1 "Bestimmung eines midregionalen Proadrenome-dullin-Teilpeptids in biologischen Flüssigkeitenzu diagno-stischen Zwecken, sowie Immunoassays far die Durchführung einer solchen Bestimmung". Assays for measuring END-r are described in applicants' European patent EP 1 564 558 B1 "Verfahren zur Bestimmung der Bildung von Endothelinen zu Zwecken der medizinischen Diagnostik, sowie Antikörper and Kits far die Durchführung eines solchen Verfahrens". The contents of both patents are hereby expressly included into the present application by reference. Examples 1 to 6 of the present application can be considered as excerpts from both patents to provide in the present application an enabling disclosure.

Both the measurable adrenomedullin and endothelin formation or release (ADM-r an END-r) are part of the relevant combined measurements according to the present invention. As relevant parameter a "ratio" of both can be defined. It is explained in more detail below.

The invention, according to one of its aspects, relates to the use of the "ratio" of ADM-r/END-r, in particular a ratio pro-adrenomedullin (pro-ADM)/pro-endothelin (pro-END) or fragments or combinations thereof, for the diagnosis of the low endothelin syndrome (LES) in critically ill patients affected by one of the diseases/conditions listed above. More specially the invention relates to the measurement of said ratio for the course control and prognosis of such disease, for the assessment of the mortality risk alone and/or in combination with a respective computer program.

In one of its preferred embodiments the invention relates to further include clinical and/or other information for the evaluation of such risk.

LES may comprise but is not limited to the association of diseases like those mentioned above.

ADM-r and END-r are normally measured by determining in suitable body fluids, especially in the circulation (serum, plasma, whole blood) a relatively persistent fragment of their physiological precursor peptides (pre-pro- or pro-peptides or -hormones). What is measured, therefore, can also be regarded as pro-peptide immunoreactivity (pro-hormone immunoreactivity). The terms pro-ADM and pro-END relate to such measurable immunoreactivity and shall comprise also amino acid sequences showing at least 75% homology, preferred at least 80% homology, more preferred at least 90% homology to pro-ADM or pro-END, their fragments or precursors.

The term diagnosis also comprises prognosis, early prognosis and course control.

Figure 1:
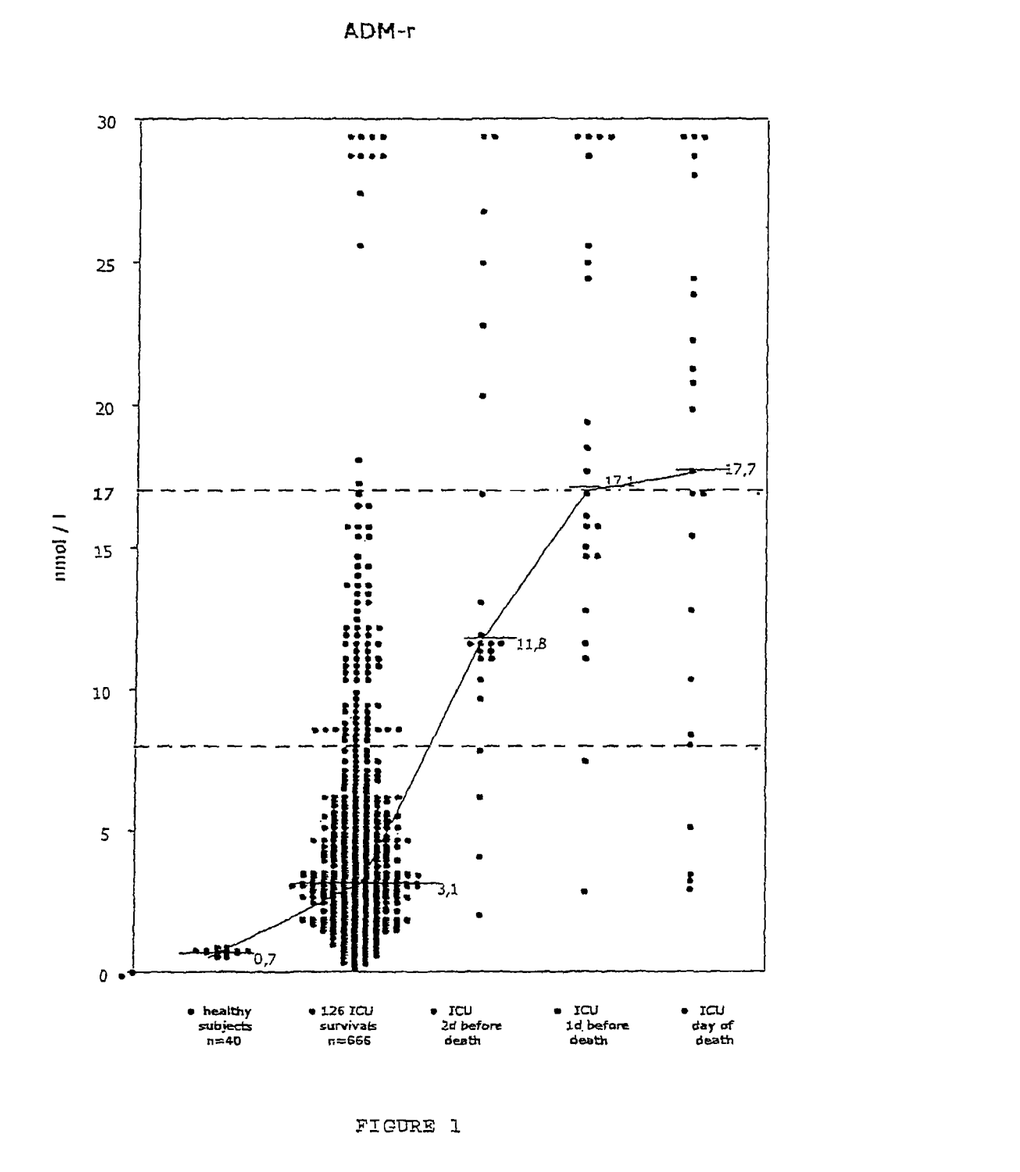
FIG. 1 shows the concentration of ADM-r in plasma of 40 healthy control individuals, 126 surviving patients at ICU and 23 patients, two days and one day before death and on the day of death.
Figure 2:
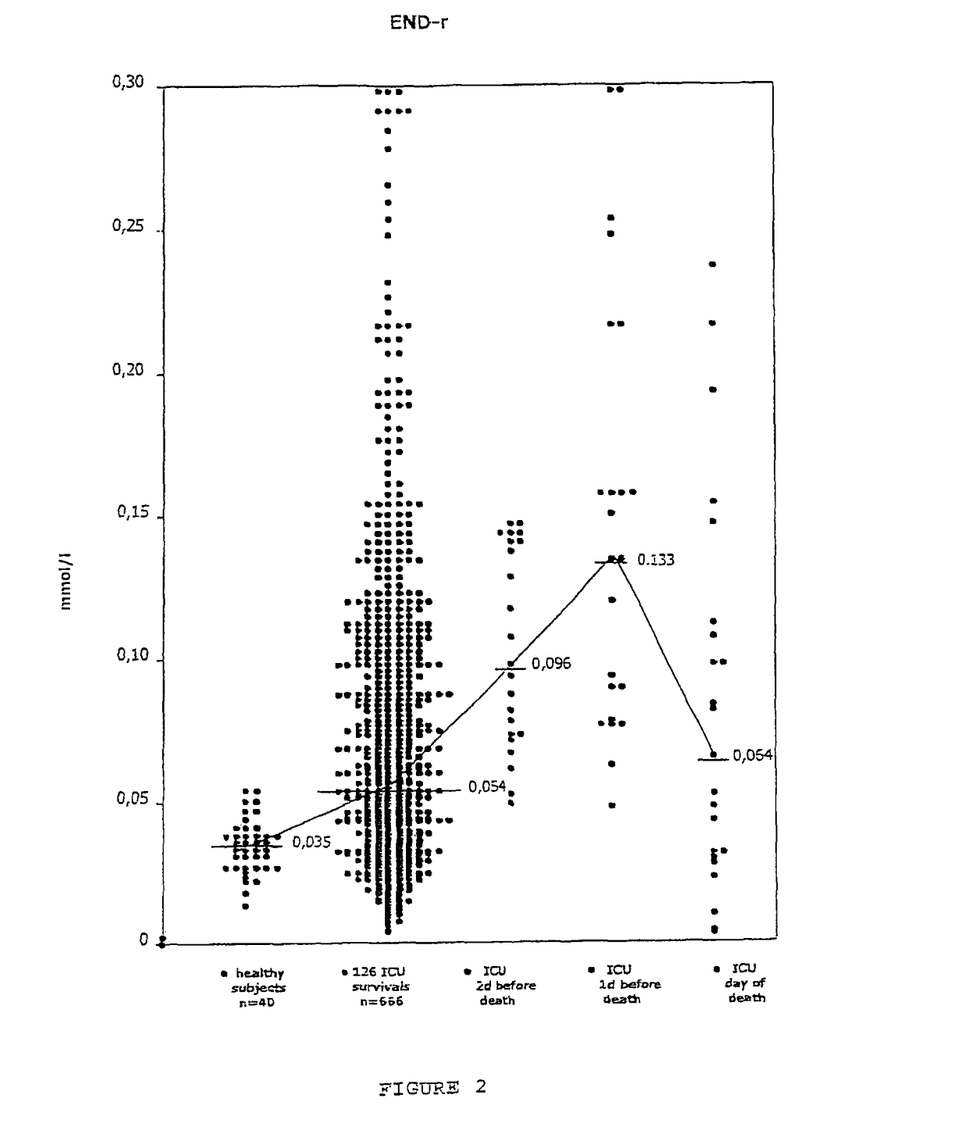
FIG. 2 shows the concentration of END-r in plasma of 40 healthy control individuals, 126 surviving patients at ICU and 23 patients, two days and one day before death and on the day of death.
Figure 3:
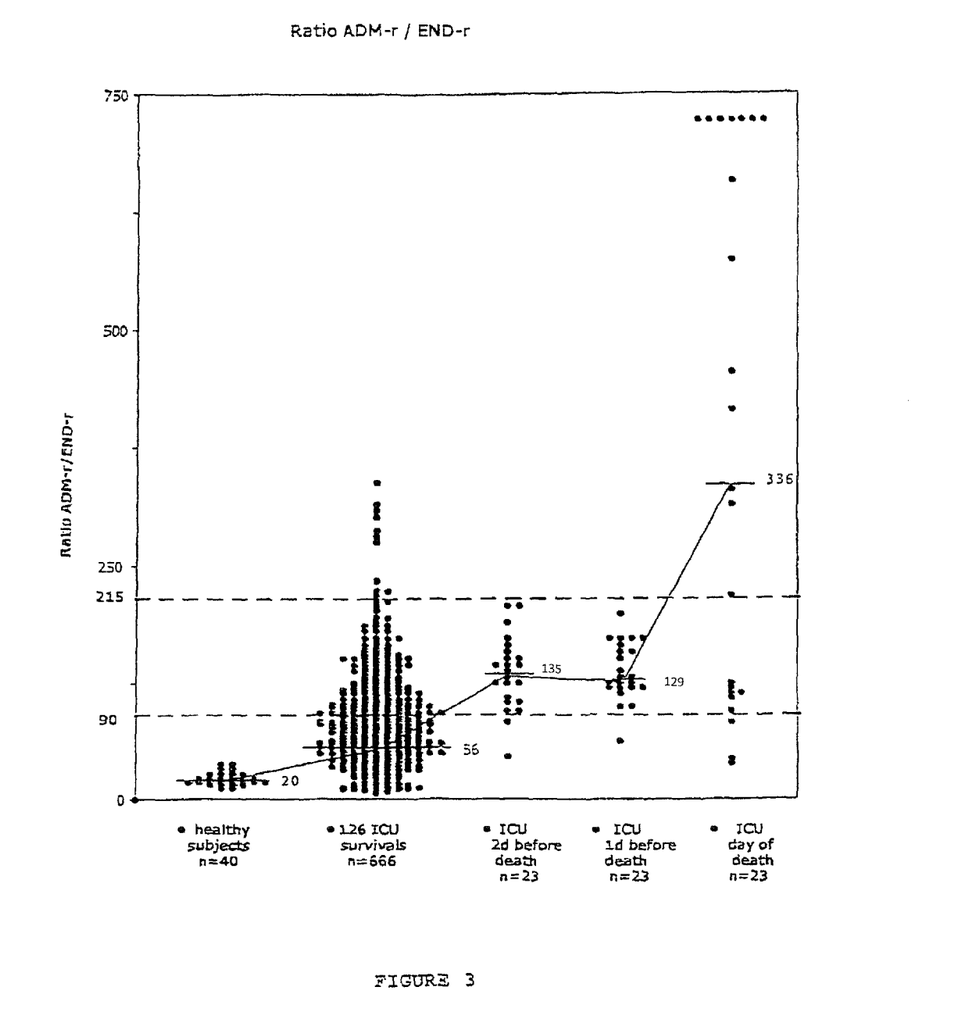
FIG. 3 shows the ratio of ADM-r/END-r in plasma of 40 healthy control individuals, 126 surviving patients at ICU and 23 patients, two days and one day before death and on the day of death.
Figure 4:
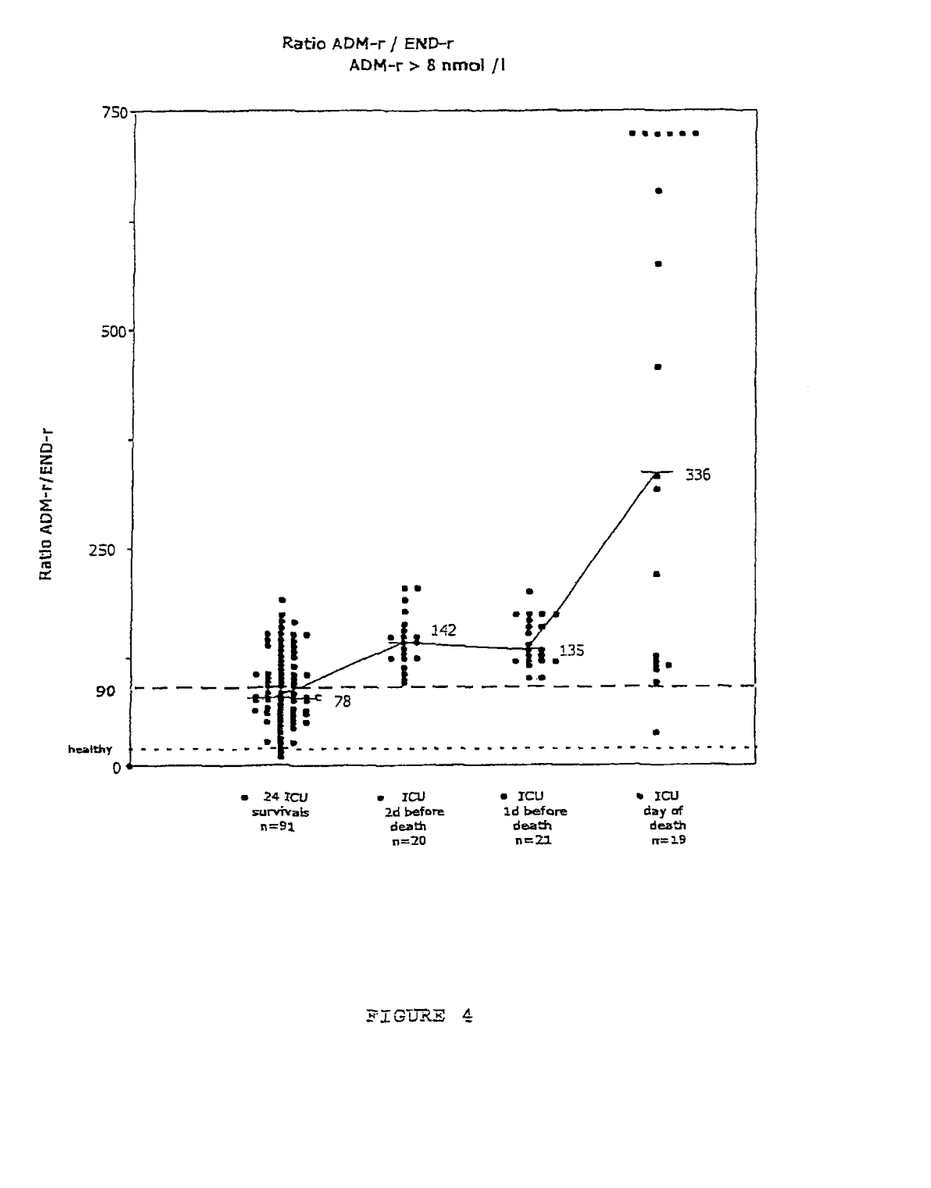
FIG. 4 shows the ratio of ADM-r/END-r including only patients having a ADM-r concentration>8 nmol/l in plasma; 24 being surviving patients at ICU and 20 further patients, two days and one day before death and on the day of death.

The invention further relates to the use of endothelin forms having vasoconstrictor activity, more particular of END-1 and/or big-END, as well as optionally of END-agonists (molecules binding to the END receptor and excerpting there the same or similar effects as the vasoactive endothelin) and/or ADM-antagonists (molecules binding to the ADM receptor and blocking there the effects as the vasoactive adrenomedullin) for the preparation of a medicament for the treatment of LES and/or diseases comprising those mentioned above. LES can be considered as an acute metabolic disorder involving an imbalance of certain potent effector molecules. By applying to a patient the active physiological molecule for re-establishing the required balance, similar to the administration of insulin to a diabetes patient, detrimental effects of a lack of said active physiological molecule can be outbalanced. The molecules involved in LES are adrenomedullin (ADM) and endothelin (END). In sepsis patients the concentrations of endothelin and adrenomedullin are increased above normal, depending on the severity of disease (FIGS. 1 and 2). In a very severe state of sepsis preceding death, according to the present invention it was surprisingly found that the concentration of endothelin decreases dramatically (FIGS. 3 and 4). This, in view of persisting high concentrations of ADM, consequently lead to a dramatic decrease in blood pressure. That dramatic decrease in blood pressure caused by the lack of endothelin (LES) frequently leads to the death of the patient as is disclosed in the present invention.

With respect to the published knowledge concerning adrenomedullin and endothelin, reference is made to the two earlier applications mentioned above. In addition, reference also is made to applicants' earliest patent application relevant for the determination of pro-ADM and pro-END in sepsis, published inter alia as WO 00/22439. The following summarizes the most important facts.

Adrenomedullin (ADM) was first described in 1993 as a new hypotensive peptide containing 52 amino acids that was isolated from a phenochromozytoma. In the same year the precursor protein pre-pro-adrenomedullin (pre-pro-ADM) containing 185 amino acids was described. The precursor protein contains a signal sequence of 21 amino acids at its N-terminus. ADM comprises the positions 95-146 of the pre-pro-ADM amino acid sequence and is a splice product thereof. Another splice product is PAMP, a 20 amino acid peptide spliced from positions 22-41 that follow the 21 amino acids of the signal peptide. The terms ADM or pro-ADM used in the present invention comprise ADM, its precursors and fragments thereof.

So far ADM and PAMP are known to influence blood pressure. ADM is a potent vasodilator, the hypotensive effect is supposed to be located in the C-terminal part of ADM. Peptide sequences at the N-terminus on the contrary show hypertensive effects. PAMP was also shown to have a hypotensive effect, even though the mechanism of action seems to be different.

In connection with the discussion of therapeutical aspects of the present application, the term "endothelin" (END) generally comprises endothelin forms with vasoconstrictor activity, especially endothelin-1 (END-1) and its precursor big-endothelin, but may also comprise related molecules as e.g. endothelin-2 (END-2) or endothelin-3 (END-3) as well as their precursors.

In connection with analytical determinations, "endothelin" generally means END-r as defined above. It is, however, within the scope of the invention to determine or monitor active forms of endothelin, i.e. especially END-1 or big-endothelin, because their decrease and finally disappearance from the circulation also is directly indicative of the onset of a critical, life-threatening crisis. Absolute values for measurable concentrations, and ratios of measurable concentrations, of course, are influenced by e.g. the molecular species actually measured, by the units in which the measurements are expressed, and by the calibration of the assays used. The absolute numerical values reported in the present application are relevant for the assays designs described herein only. Since they may have to be adapted if e.g. another analyte is measured or the particulars of its determination are changed, it is not practical to express the results of the present invention in absolute numerical values. However, by following the teachings of the present application, including the described scoring of the measured results, the skilled person can easily determine the numbers and ratios relevant for any modified determination method.

Endothelin-1 comprises 21 amino acids and is the most potent vasoconstrictor known. 3 isoforms of END are existing: endothelin-1 (END-1), endothelin-2 (END-2) and endothelin-3 (END-3), END-1 is present in the highest concentrations and is the most potent. Endothelin-1 is synthesized in the endothelial cells, in lung, heart, kidney and brain. The primary translation product of the human endothelin-1 gene is pre-proendoethelin-1, comprising 212 amino acids. In the secretory pathway the signal peptidase removes the short N-terminal signal sequence, comprising 17 amino acids. The resulting pro-endothelin is subsequently processed to a still biologically inactive big-endothelin, comprising 38 amino acids, by the protease furin, which can be found in the circulation. The mature biologically active endothelin-1 is formed from big-endothelin by endothelin converting enzyme. Endothelin exerts its biological effect by binding to specific receptors that are localized on muscle cells, myocytes and fibroblasts. This binding causes the efflux of calcium, activation of phopholipase C and inhibition of Na/K ATPase. Besides the vasoconstrictive effect, endothelin also regulates growth.

The concentration of ADM in the blood circulation and other biological fluids is increased significantly in a variety of diseases like congestive heart failure, myocardiac infarction, renal diseases, high blood pressure, diabetes mellitus, in the acute phase of shock, sepsis, septic shock, multiple organ failure. PAMP concentrations are also increased in some of the above mentioned diseases/disorders, however the plasma level is decreased relatively to ADM. It is known that in sepsis and septic shock unusually high concentrations of ADM are observed. This finding is related to the hemodynamic changes that are typical for the course of disease in patients with sepsis and other severe diseases like SIRS.

Increased plasma concentrations of endothelin-1 and big-endothelin were shown for several diseases comprising cardiovascular diseases comprising pulmonary hypertension, artherosclerosis, congestive heart failure, cardiac infarction, sepsis, septic shock and cancer.

A major cause of mortality due to sepsis is the so-called multiple organ failure, which is caused by a systemic vasodilation, including a decrease of blood pressure and a loss of priority supply of single organs and tissues. Endothelin is thought to play a role in the degree of severity of sepsis and to play a role in the mortality of sepsis.

Analytical/Diagnostic Aspects of the Invention

The present invention in one of its aspects relates to the diagnosis of LES and/or associated diseases comprising those mentioned above. The present invention further relates to the concomitant determination of the levels of END-r and ADM-r, more specially of pro-END and pro-ADM and/or their fragments. The combined measurement enables the calculation of a ratio and/or an algorithm and the use of such a derived ratio and/or algorithm for the diagnosis, prediction, prognosis of course of severity and the risk of mortality of LES and/or the above mentioned diseases (FIGS. 1 and 2).

The invention is based on the surprising finding that both values of pro-ADM and pro-END are increasing in patients during course of disease, wherein the values of pro-ADM are increasing more than those of pro-END, leading to an increase of the overall ratio pro-ADM/pro-END until one day before exit.

More remarkably, however, the concentration of endothelin on the day of death decreases dramatically. Consequently the ratio and/or algorithm of pro-ADM/pro-END increases dramatically (FIGS. 3 and 4).

The determination of ADM, more specially ADM-r, as well as END, more specially END-r, therefore provides information on the health state of a critically ill patient, especially with respect to the development of a life threatening crisis which requires an intervention. This is explained more completely referring to the following analytical findings and the results shown in Table 1 (see Example 8) and the Figures:

149 patients were included in a study, who were admitted to an intensive care unit (ICU) and developed a sepsis during their stay at ICU.

EDTA-plasma of the patients was gained at each day of their stay at ICU (3-29 days). The plasma was stored at −20° C. until further use.

Pro-ADM and pro-END values were determined by using a coated tube assay as described in the earlier European patents of the applicant already mentioned above. For the assays, synthesized peptides were used to produce antigens and injected into animals to raise antibodies against the different peptides as described earlier. In a preferred embodiment the peptides were linked to the carrier protein keyhole limpet hemocyanin using MBS (m-maleimidobenzoyl-N-hydroxysuccinimid ester) and used for the immunisation of sheep.

More particular, amino acid sequences of partial peptides 83-94 [SSPDAARIRVKR=Sequence ID 2] and 69-86 [RPQDMKGASRSPEDSSPD=Sequence ID 3] of pre-pro-ADM 1-185 [Sequence ID 1] as well as partial peptide 168-181 [RSSEEHLRQTRSET=Sequence ID 6] and 200-212 [SRERYVTHNRAHW=Sequence ID 7] of pre-pro-END 1-212 [Sequence ID 5] were synthesized. These sequences are comprised in the pre-pro-ADM 1-185 and pre-pro-END 1-212. An amino terminal cystein residue was added to each peptide. The peptides were conjugated to a hemocyanin and antibodies were produced to the above mentioned peptides in sheep as described earlier. Polyclonal antibodies were raised against the above mentioned peptides. Antibodies were purified. In a preferred embodiment, this was achieved by ligand specific affinity chromatography by coupling the peptides via the amino terminal cystein residue to SulfoLink-Gel of Pierce (Boston, USA) according to the methods of Pierce. The antibodies further were tagged with a marker to enable detection. The marker used is preferably a luminescent marker and yet more preferred a chemiluminescent marker as described earlier.

Methods for the detection of binding of the antibody to the respective molecule are known by the person skilled in the art comprising sandwich immuno assays, radio immuno assays, ELISA or point of care tests. Preferably, according to the invention the binding of the antibody to the target is detected by chemiluminescence.

The detection and the determination of the concentration of pro-ADM and pro-END can be conducted in various body fluids, tissues and other biomaterials but preferably is conducted in serum or plasma. It can take place in various states of all kinds of diseases as exemplified above which may lead to LES, sepsis, septic shock, SIRS and related severe conditions.

It is part of the invention to use the correlation of ADM-r and END-r, preferably of precursor proteins with pro-ADM and pro-END immunoreactivity, or, if feasible, also of the mature proteins like END and ADM in the state of disease/disorder in body fluids, tissues or other biomaterials, blood, plasma and liquor in particular.

The invention further uses the significant change of precursor protein concentrations in body fluids, tissue and other biomaterials in disease or disorder, in particular in a severe state of disease accompanied by LES as acute complication.

AMD-r, if measured as described herein, is present in plasma of healthy individuals at concentrations of <1 nmol/l (median: 0.7). Critically diseased persons who survived a sepsis show a significantly increased ADM-r concentration (median 3.1). The median of dying patients is significantly increased as compared to the group of surviving patients (median 11.8/17.1/17.7; 2 days before exit/one day before exit/on the day of death respectively, FIG. 1).

The concentration of END-r as a putative antagonist of ADM, if measured as described herein, increases from a median of 0.035 nmol/l plasma to 0.054 nmol/l in surviving patients. The concentration in dying patients further increases to 0.096 and 0.133 nmol/l two days before exit and one day before exit respectively. But surprisingly the concentration of END-r decreases dramatically on the day of death (median 0.064 nmol/l, FIG. 2).

These findings can be correlated with the prognosis of survival in a severe state of LES or other diseases comprising those mentioned above by determining the concentration of ADM-r, END-r and combinations thereof and forming, as additional parameter, a ratio of the above mentioned proteins and/or an algorithm thereof.

Firstly, the concentration of ADM-r alone was used to determine the prognosis of survival (Table 1 and FIG. 1). Column (specificity) shows the number of surviving patients having a concentration of less than 17 nmol/l serum/plasma of ADM-r, i.e. 117 of 126 patients have a concentration of less than 17 nmol/l, 102 patients a concentration of less than 8 nmol/l. Thus AMD-r shows a specificity of 93% for survival at a cut off at 17 nmol/l and 81% at a cut off at 8 nmol/l.

The sensitivity of mortality is determined in the following way: 23 patients died during their stay at ICU. At a cut off value of 17 nmol/l of ADM-r six patients (26%=sensitivity of mortality) showed concentrations above 17 nmol/l two days before exit, 12 patients (52%) one day before exit and 13 patients (57%) on the day of death. At a cut off value at 8 nmol/l, 19 (83%) of 23 patients showed concentrations above 8 nmol/l of ADM-r two days before exit, 21 patients (91%) one day before exit and 19 patients (83%) on the day of death (Table 1; see Example 8).

Thus a cut-off value at 8 nmol/l of ADM-r (i.e. excluding the patients having a concentration below 8 nmol/l of ADM-r) includes most of the patients who died during their stay at ICU.

Further, as has been found by the inventors, the ratio of ADM-r/END-r according to the present invention forms an additional parameter of high validity in connection with the prognosis of septic patients in ICUs.

Surprisingly said ratio increases during the course of disease and even more surprisingly the ratio increases dramatically on the day of death. According to the results, the specificity and sensitivity of survival and mortality respectively of LES and various other diseases comprising those mentioned above are disclosed, as well as the prognosis of severity of disease and mortality risk.

Measured ratios of AMD-r/END-r are shown in Table 1 and FIG. 3. The ADM-r/END-r ratio in healthy individuals has a maximum value of about 50 (median 20). The median of surviving patients at ICU is increased to 56. Significant further increases can be observed two days (median 135) and one day (median 129) before exit and a surprisingly dramatic increase on the day of death at a median of 336. The prognosis at a specificity of 76% (Table 1, i.e. patients included having a concentration of ADM-r of less than 43 nmol/l) is 91% two days before exit, 96% one day before exit and 87% on the day of death (Table 1 and FIG. 3). At a higher specificity of 93%, (i.e. patients included having a concentration of ADM-r of less than 18 nmol/l), a prognosis is only possible on the day of death having a sensitivity of 61% (Table 1).

It can surprisingly be deduced from the results that the threatening of life in LES is only present at high ADM-concentrations, as a high potential of vasodilation must be reached. High concentrations of ADM are only tolerated if they are outbalanced by the respective END concentration.

For a further analysis of the results, the patients were further selected:
1. according to the AMD-r-concentration (>8 nmol/l) and
2. according to the ratio of ADM-r/END-r (FIG. 4).

It was shown that a high portion of surviving patients with an ADM-r concentration>8 nmol/l at one day of their stay at the ICU, N=24 had a ratio of less than 90 (N=15) and thus their survival was assured. According to that assumption however also the dying patients would be included with a high probability 2 days before their death (sensitivity 87% two days before exit/91% one day before exit/78% on the day of death). Taking into account the sum of patients included in the study (126 surviving patients) the specificity surprisingly is as high as 93%.

The sequential analysis of ADM-r, END-r and the ratio and/or the algorithm of ADM-r/END-r at an equally high specificity (93%) surprisingly shows a higher sensitivity for the prognosis (87%/91%/78%) than the analysis of ADM-r alone (26%/52%/57%) or ratio alone (0/0/61) (values 2 days before death/1 day before death/day of death respectively). The invention, consequently, also relates to the detection, early detection, determination of severity, course control and prognosis of the diseases/disorders mentioned above using said ratio or the determined algorithm.

In this context the invention contemplates the use of a computer program to use the data received from the ratio for the detection, early detection, determination of severity, course control and prognosis of LES and/or the diseases mentioned above.

For carrying out measurements as discussed above, assays for ADM-r and END-r, as they are described in applicants' European patents mentioned above, and the corresponding kits, can be used with advantage.

Therapeutical Aspects of the Invention

In contrast to the state of the art, the invention discloses the surprising finding that elevated concentrations of endothelin (especially if determined as END-r) are beneficial for a patient having highly elevated concentrations of ADM-r as they are typically found in patients in severe conditions as e.g. sepsis and the related diseases mentioned above. In other words, the results show that high levels of END-r enable a patient to tolerate high, otherwise deadly levels of ADM-r typical for conditions as sepsis so that death can be prevented. Shortly, high ADM levels apparently can be outbalanced by physiological END levels of sufficient height.

A measurable decrease of END-r, or serum END, in such critically ill patient constitutes a clear clinical sign indicating a high risk of death of patients having high levels of ADM-r. The observed sharp decrease of measurable END-r and END respectively may be interpreted as sign of an exhaustion of the cellular reservoirs of END precursors under the physiological stress of a condition as sepsis, or of an inability of the physiological, molecular machinery producing END and its precursors to keep up with the parallel continuing production of ADM and/or to outbalance the continuing vasodilatory action of high ADM concentrations.

According to a first therapeutical aspect the invention contemplates the administration of vasoconstrictive endothelin forms, especially of END-1 and/or big-END, to critically ill patients having high measured levels of ADM-r to externally replenish the active END in such patients. "Vasoconstrictive endothelin forms" are intended to include directly acting endothelin forms as END-1, as well as precursors as big-END which as such are inactive but are readily converted to an active form when they are introduced into the circulation of a human patient.

The administration of endothelin, in clinical settings as e.g. in ICUs (intensive care units), can be preceded by an analysis of the actual concentrations of ADM-r, END-r and a determination of the "ratio" discussed above. However, such preceding measurement and analysis must not be considered as an indispensable pre-requisite for the administration of endothelin according to the present invention.

In health care settings, e.g. in an ICU, there may not be enough time to wait for results of measurements of biomolecules as e.g. ADM-r and END-r before a decision regarding a therapeutic intervention can be made. It is, therefore, within the scope of the present invention to administer active endothelin to critically ill patients in response to characteristic changes of other physiological parameters which are indicative of the underlying low endothelin syndrome (LES). Such parameters may be measurements of physiological variables as blood pressure, body temperature, pulse frequency and similar parameters as they are used to monitor the state of a septic patient. Knowing the beneficial effect of an administration of endothelin, such administration can be effected on the basis of purely empirical clinical data.

It is, however, also within the scope of the present invention to administer endothelin in response to a quantitative or semi-quantitative measurement of ADM-r alone, i.e. when the ADM level gets critically high. In view of the requirement to take a quick decision, it may be preferable to conduct the determination of ADM-r in ICUs with POC (point-of care) measuring devices, e.g. devices of the immunochromatographic type or devices with electrochemical probes quickly producing readings for the concentration of interest, to obtain an at least semiquantitative reading allowing an evaluation of the actual levels of ADM-r in a patient and to make a decision for the intravenous administration of endothelin. Suitable POC measuring devices are well known to the skilled person. An example for a suitable design is the rapid test device PCT-Q® obtainable from B.R.A.H.M.S Aktiengesellschaft for the rapid POC determination of procalcitonin (PCT) e.g. in a hospital setting.

It is further within the scope of the present invention to administer endothelin to patients which are continuously monitored for the concentration(s) on one or more of the relevant biomolecules, or other relevant clinical parameters.

As stated earlier, in a therapeutical context "endothelin" means endothelin forms with vasoconstrictor activity, especially endothelin-1 (END-1) and its precursor big-endothelin, but the term may also extend to related molecules of similar activity, as e.g. endothelin-2 (END-2) or endothelin-3 (END-3) as well as their precursors.

The administration of the most active, directly acting END-1 at the moment is regarded as being preferred in critical care situations. Preferably such administration is an intravenous administration by infusion or injection, using a liquid formulation (solution or dispersion) containing a suitable concentration of END-1 together with pharmaceutically acceptable carriers etc. Such liquid formulation (medicament) can contain all pharmaceutically acceptable and useful excipients, stabilisers and other ingredients suitable for such type of administration and for maintaining a stable condition within the administered formulation for the time of infusion.

It is, further, within the scope of the invention to administer, or co-administer, slower acting forms of endothelins, for example admixtures of quick acting and slower acting forms. Slower acting forms, e.g. in the form of big-END, may provide a more uniform pharmacokinetic profile and a longer lasting action of endothelins. Such forms may be more suitable for injection, while directly acting forms are preferred for administration by infusion.

It is further within the scope of the present invention to administer agonists of endothelin in place of, or together with, vasoconstrictive endothelins to achieve special effects, e.g. a favourable pharmacokinetic profile, or to assist the patient in situations when the most critical acute phase is has been survived.

Further, since the life-threatening influence for the patient is not the lack of endothelin per se but the vasodilating action of high concentrations of ADM (ADM-r), it is also within the scope of the invention to use, in place of endothelin and/or endothelin agonists, or in combination therewith, adrenomedullin antagonists, i.e. molecules which prevent or attenuate the vasodilating action of adrenomedullin, e.g. by blocking its relevant receptors, or substances preventing the binding of adrenomedullin to its receptor (e.g. specific binders as e.g. antibodies binding to adrenomedullin and blocking its receptor bindings sites; "immunological neutralisation"). Such use, or combined use, including a subsequent or preceding separate use, may in certain cases be desirable for example to improve the therapeutic success, or to avoid undesirable physiological stress or side effects.

The invention further discloses the use of endothelin forms with vasoconstrictor activity, more specially END-1 and/or big-END, as well as END agonists, for the preparation of a medicament for the treatment of LES and other conditions and diseases comprising those mentioned above. In particular, endothelin-1, big-endothelin and/or any endothelin 1 receptor agonists are used as active ingredients to prepare medicaments for administering them to a critically ill patient. Preferably the medicament is a liquid formulation for intravenous administration by infusion, for example via a catheter, or by injection.

There do not seem to exist, in the available scientific literature, proposals to use vasoconstrictive endothelin for medical purposes. The claimed use, therefore, apparently can be considered as first medical use.

In medicaments as discussed above the mentioned active END may be used, as is customary in the art, in liquid formulations containing suitable concentrations of e.g. appropriate carriers, stabilizers, nutrients, electrolytes, dissolved salts, osmotic agents for providing isotonic conditions, buffers and/or solvents and other adjuvants and excipients suitable for administration in a patient.

EXAMPLE 1—PEPTIDE SYNTHESIS

An N-terminal cystein residue was added to synthesized Peptides of human pro-ADM and pro-END. They were purified using mass spectrometry and the quality controlled using reversed phase HPLC and lyophiliysed in aliquots (Jerini AG, Berlin, Germany) according to standard procedures known to the person skilled in the art.

EXAMPLE 2—CONJUGATION AND IMMUNIZATION

Peptides of Sequence IDs 2, 3, 6 and 7 were conjugated to the carrier protein KLH (keyhole limpet hemocyanin) by MBS (Maleimid-obenzoyl-N-hydroxysuccinimid ester) according to the protocols for "NHS-esters-maleimide crosslinkers" by PIERCE, Rockford, Ill., USA. Sheep were immunized receiving 100 μg of conjugate (μg according to the peptide content of the conjugate). Starting at month 4 after immunization every four weeks 700 ml of blood were withdrawn from every sheep and antiserum was gained by centrifugation. Conjugation, immunizations and production of antisera were done by MicroPharm, Carmerthenshire, UK.

EXAMPLE 3—PURIFICATION OF ANTIBODIES

The polyclonal antibodies from sheep were purified using ligand specific affinity purification. For that step the Cys(0)-peptides were linked to SulfoLink-Gel supplied by Pierce (Boston, USA). The binding occurred according to the protocol of Pierce. 5 mg of peptide were added per 5 ml of gel.

In summary, columns were washed three times with 10 ml elution buffer (50 mM citric acid, pH 2.2) and binding buffer (100 mM sodium phosphate, 0.1% Tween, pH 6.8). 100 ml of sheep antiserum were filtered using a filter diameter of 0.2 μm and added to the column material. The gel was eluted quantitatively with 10 ml binding buffer. The material was incubated over night at room temperature by gentle rotation. The material was transferred to empty columns (NAP 25, Pharmacia, emptied). The eluates were discarded. Subsequently the columns were washed with 250 ml protein-free binding buffer (protein content of washed eluate<0.02 A280 nm). Elution buffer was added to the washed columns and fractions of 1 ml were collected. The protein content of each fraction was determined by the BCA-method (according to the protocol of PIERCE, Rockford, Ill., USA). Fractions of a protein content>0.8 mg/ml were pooled.

EXAMPLE 4—TAGGING

500 μl of affinity purified antibodies generated against the peptides of Sequence IDs 2, 3, 6 and 7 were rebuffered in 1 ml 100 mM potassium phosphate buffer (pH 8.0) was re-buffered via a NAP-5 gel filtration column (Pharmacia) according to the protocol of Pharmacia.

For the tagging with a chemiluminescent marker 10 μl of MA70-Akridinium-NHS-ester (1 mg/ml; Hoechst Behring) were added to 67 μl of antibody solution and incubated for 15 minutes at room temperature. The solution was rebuffered in 1 ml solvent A (50 mM potassium phosphate, 100 mM NaCl, pH 7.4) in a NAP-5 gel filtration column according to the protocols of Pharmacia, particles of low molecular weight were eluted. For elution of unbound labels a gel filtration HPLC was done (Column: Waters Protein Pak SW300). The sample was added and chromatographs at a flow rate of 1 ml/minute in solvent A. The sample was measured at wave length of 280 and 368 nm to determine the degree of tagging. The absorption ratio 368/280 nm had a peak of 1.0. The fractions containing monomeric antibodies were collected (retention time 8-10 minutes) and taken up in 3 ml 100 mM sodium phosphate, 150 mM NaCl, 5% bovine serum albumin, 0.1% sodium azide, pH 7.4).

The tagged antibody was used in a sandwich assay as well as in different assays like SPALT-assays.

EXAMPLE 5—COUPLING

For a sandwich-assay the purified antibodies against the peptides of Sequence IDs 2, 3, 6 and 7 were immobilized on irradiated polystyrol tubes (Greiner, Germany). For that procedure the antibody solutions were diluted to a protein concentration of 6.7 μg/ml with 5.0 mM Tris, 100 mM NaCl, pH 7.8. 300 .mu.l of diluted protein solution per tube were pipetted. These were incubated for 20 hours at room temperature, the solution was removed. Then 4.2 ml of a 10 mM sodium phosphate, 2% Karion FP, 0.3% bovine serum albumin, pH 6.5 solution were added to each tube. After 20 hours the solution was removed and the tubes dried in a vacuum drier. The procedure can also be done as inverse sandwich assay according to procedures known to a person skilled in the art.

EXAMPLE 6—SANDWICH IMMUNOASSAY

The following assay buffer was used: 100 mM sodium phosphate, 150 mM NaCl, 5% bovine serum albumin, 0.1% unspecified sheep IgG, 0.1% sodium azide, pH 7.4.

The protein content of EDTA-plasma of healthy individuals and patients of various diseases/diseases mentioned above was determined.

In the tubes containing the immobilized antibody EDTA-plasma of patients was pipetted (10 μl ADM and 50 μl END-r). 200 μl of PBS (phosphate buffered saline), 0.1% bovine serum albumin were added to each tube and incubated at room temperature for 2 hours. After washing 3 times with 4 ml PBS 200 μl acridiniumester-tagged polyclonal sheep antibody (affinity purified, raised against the peptide 83-94 [Sequence ID 2] and 69-86 [Sequence ID 3] of pre-pro-ADM 1-185 as well as partial peptide 168-181 [RSSEEHLRQTRSET=Sequence ID 6] and 200-212 [SRERYVTHNRAHW=Sequence ID 7] of pre-pro-END 1-212, 20 ng each in PBS, 0.1% bovine serum albumin) respectively. After further incubation of 2 hours at room temperature unbound tagged antibodies are removed by washing 5 times with 2 ml PBS each. Tagged antibody bound to the tube was quantified by measuring the luminescence in a luminometer (Berthold LB 952T/16).

The individual values measured were quantified according to a usual calibration curve that was established using defined dilutions of synthesized pre-pro-ADM 45-92 and pre-pro-END 169-212 as standard solutions.

EXAMPLE 7—MEASUREMENTS

Concentrations of ADM-r and END-r in Healthy Individuals and State of Disease 149 patients were included in the study who were at the intensive care unit for different reasons and who developed a sepsis during their stay at the intensive care unit (criteria: www.talessin.de/scripte/medizin/sepsis1.html). Every day during their stay at the intensive care unit (3-29 days) EDTA-plasma of the patients was obtained and stored at −20° C. until further use.

ADM-r is present in plasma of healthy individuals at concentrations of <1 nmol/l (median: 0.7). Critically diseased persons who survived a sepsis show a significantly increased ADM-r concentration (median 3.1). The median of dying patients is significantly increased as compared to the group of surviving patients (median 11.8/17.1/17.7; 2 days before exit/one day before exit/on the day of death respectively, FIG. 1).

The concentration of END-r (pro-END) as a putative antagonist of ADM increases from a median of 0.035 nmol/l plasma to 0.054 nmol/l in surviving patients. The concentration further increases to 0.096 and 0.133 nmol/l two days before exit and one day before exit respectively. Surprisingly the concentration of END-r decreases dramatically on the day of death (median 0.064 nmol/l, FIG. 2).

EXAMPLE 8—EVALUATIONS

ADM-r and the Prognosis for Severity of Disease/Disorder

The concentration of ADM-r was used to determine the prognosis of survival (Table 1 and FIG. 1). Column 2 of Table 1 (specificity) shows the number of surviving patients having a concentration of less than 17 nmol/l plasma of ADM-r, i.e. 117 of 126 patients have a concentration of less than 17 nmol/l, 102 patients a concentration of less than 8 nmol/l. Thus ADM-r shows a specificity of 93% for survival at a cut off at 17 nmol/l and 81% at a cut off at 8 nmol/l. The sensitivity of mortality is determined in the following way: 23 patients died during their stay at ICU. At a cut off value of 17 nmol/l of ADM-r six patients (26%=sensitivity of mortality) showed concentrations above 17 nmol/l two days before exit, 12 patients (52%) one day before exit and 13 patients (57%) on the day of death. At a cut off value at 8 nmol/l, 19 (83%) of 23 patients showed concentrations above 8 nmol/l of ADM-r two days before exit, 21 patients (91%) one day before exit and 19 patients (83%) on the day of death (Table 1).

Thus a cut-off value at 8 nmol/l of ADM-r, i.e. excluding the patients having a concentration below 8 nmol/l of ADM-r, includes most of the patients who died during their stay at ICU.

TABLE 1

| | Specificity Survivals n = 126 | Sensitivity | | |
| --- | --- | --- | --- | --- |
| | | 2nd day-before death n = 23 | Last day before death n = 23 | day of death n = 23 |
| ADM-r | | | | |
| Cut off 17 nmol/l | 117 | 6 | 12 | 13 |
| Cut off 8 nmol/l | 102 | 19 | 21 | 19 |
| Ratio ADM-r/END-r | | | | |
| Cut off 215 | 117 | 0 | 0 | 14 |
| Cut off 90 | 96 | 21 | 22 | 20 |
| Ratio ADM-r/END-r | | | | |
| ADM-r >8 nmol/l Cut off 90 | 117 | 20 | 21 | 18 |

| | Specificity Survivals | Sensitivity | | |
| --- | --- | --- | --- | --- |
| | | 2nd day before death | Last day before death | day of death |
| ADM-r | | | | |
| Cut off 17 nmol/l | 93% | 26% | 52% | 57% |
| Cut off 8 nmol/l | 81% | 83% | 91% | 83% |

TABLE 1-continued

| Ratio ADM-r/END-r | | | | |
| --- | --- | --- | --- | --- |
| Cut off 215 | 93% | 0% | 0% | 61% |
| Cut off 90 | 76% | 91% | 96% | 87% |
| Ratio ADM-r/END-r | | | | |
| ADM-r >8 nmol/l Cut off 90 | 93% | 87% | 91% | 78% |

EXAMPLE 9—RATIO

Ratio ADM-r/END-r

The ratio of ADM-r/END-r is shown in Table 1 and FIG. 3. The ADM-r/END-r ratio in healthy individuals has a maximum value of about 50 (median 20). The median of surviving patients at ICU is increased to 56. Significant further increases can be observed two days (median 135) and one day (median 129) before exit and a surprisingly dramatic increase on the day of death at a median of 336. The prognosis at a specificity of 76% (Table 1, i.e. patients included having a concentration of ADM-r of less than 43 nmol/l is 91% two days before exit, 96% one day before exit and 87% on the day of death (Table 1 and FIG. 3). At a higher specificity of 93%, i.e. patients included having a concentration of ADM-r of less than 18 nmol/l, a prognosis is only possible on the day of death having a sensitivity of 61% (Table 1).

EXAMPLE 10—RATIO ADM-R/END-R INCLUDING PATIENTS HAVING A CONCENTRATION OF ADM-R ABOVE 8 NMOL/L

Thus the patients were further selected according to the ADM-concentration (>8 nmol/l) and according to the ratio of ADM-r/END-r (FIG. 4).

It was shown that a high portion of surviving patients with an ADM concentration>8 nmol/l at one day of their stay at the ICU, N=24 had a ratio of less than (N=15) and thus their survival was assured. According to that assumption however also the dying patients would be included with a high probability 2 days before their death (sensitivity 87% two days before exit/91% one day before exit/78% on the day of death). Taking into account the sum of patients included in the study (126 surviving patients) the specificity surprisingly is as high as 93%.

Thus the sequential analysis of ADM-r, END-r and the ratio and or algorithm of ADM-r/END-r at an equally high specificity (93%) surprisingly shows a higher sensitivity for the prognosis (87%/91%/78%) as the analysis of ADM (26%/52%/57%) or ratio (0/0/61) in their own (values 2 days before death/one day before death/day of death respectively).

The invention claimed is:

1. A method of treating a critically ill human patient admitted to an intensive care unit (ICU), comprising:
    determining the concentration, in particular concentration units, of a pro-adrenomedullin (pro-ADM) molecule and/or one or more physiologically occurring fragments thereof using a plasma sample from the patient in an in vitro selective immunodiagnostic assay recognizing a physiologically occurring fragment that is not the mature ADM,
    determining the concentration in said concentration units, of a pro-endothelin (pro-END) molecule and/or one or more physiologically occurring fragments thereof using a plasma sample from the patient in an in vitro selective immunodiagnostic assay recognizing a physiologically occurring fragment that is not the mature END,
    wherein the immunodiagnostic assays use combinations of antibodies comprising antibodies against peptides having the amino acid sequences according to SEQ ID NO: 2 or 3 for pro-ADM and SEQ ID NO: 6 or 7 for pro-END,
    calculating the ratio of the pro-ADM concentration to the pro-END concentration, and when the ratio in said patient is above a cut off value of 90, and when the concentration of pro-ADM is >8 nmol/l or an equivalent value according to the determination method employed, administering to the patient an antibody that binds to ADM and blocks its receptor binding sites, in an amount sufficient to reduce the ratio to below the cut off value.

2. The method according to claim 1, wherein the patient is admitted to an intensive care unit with a diagnosis of one or more of sepsis, SIRS, septic shock, multiple organ failure, infections systemic or local, bacterial infections, heart disease, peritonitis, pancreatitis, local and/or systemic inflammation, meningitis, trauma, ruptured aortic aneurysm, intoxication, endotoxemia, anuria, renal insufficiency, arterial hypertension, pulmonary hypertension, atherosclerosis, cancer, congestive heart failure, cardiovascular disease, coronary artery disease, ischemia, antiarrhythmic effects, cancer comprising colorectal cancer, renal and/or heart failure or organ injury.

3. The method according to claim 1, wherein at least one of the antibodies that specifically binds said physiologically occurring fragment of pro-ADM or pro-END is immobilized onto a solid phase and at least one second antibody specifically binds another part of the same fragment and is used for detection of the fragment attached to the solid phase.

4. The method of claim 1, wherein said antibody that binds to ADM is administered by infusion or injection.

5. The method of claim 1, wherein said antibody that binds to ADM is administered with a pharmaceutically acceptable liquid carrier and one or more of stabilizers, nutrients, electrolytes, dissolved salts, osmotic agents for providing isotonic conditions, buffers and/or solvents and/or other adjuvants and excipients suitable for intravenous administration.

* * * * *

SEQUENCE LISTING

<160> NUMBER OF SEQ ID NOS: 8

<210> SEQ ID NO 1
<211> LENGTH: 185
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Ser Ser Pro Asp Ala Ala Arg Ile Arg Val Lys Arg
1               5                   10
```

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Arg Pro Gln Asp Met Lys Gly Ala Ser Arg Ser Pro Glu Asp Ser Ser
1               5                   10                  15

Pro Asp
```

<210> SEQ ID NO 4
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

-continued

Asn Lys Trp Ala Leu Ser Arg Gly Lys Arg Glu Leu Arg Met Ser Ser
1               5                   10                  15

Ser Tyr Pro Thr Gly Leu Ala Asp Val Lys Ala Gly Pro Ala Gln Thr
            20                  25                  30

Leu Ile Arg Pro Gln Asp Met Lys Gly Ala Ser Arg Ser Pro Glu Asp
        35                  40                  45

Ser Ser Pro Asp Ala Ala Arg Ile Arg Val
    50                  55

<210> SEQ ID NO 5
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Glu Glu His Leu Arg Gln Thr Arg Ser Glu Thr
1               5                   10

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Arg Glu Arg Tyr Val Thr His Asn Arg Ala His Trp
1               5                   10

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Leu Glu Asn Leu Leu Pro Thr Lys Ala Thr Asp Arg Glu Asn Arg
1               5                   10                  15

Cys Gln Cys Ala Ser Gln Lys Asp Lys Lys Cys Trp Asn Phe Cys Gln
                20                  25                  30

Ala Gly Lys Glu Leu Arg Ala Glu Asp Ile Met Glu Lys Asp Trp Asn
            35                  40                  45

Asn His Lys Lys Gly Lys Asp Cys Ser Lys Leu Gly Lys Lys Cys Ile
        50                  55                  60

Tyr Gln Gln Leu Val Arg Gly Arg Lys Ile Arg Arg Ser Ser Glu Glu
65                  70                  75                  80

His Leu Arg Gln Thr Arg Ser Glu Thr Met Arg Asn Ser Val Lys Ser
                85                  90                  95

Ser Phe His Asp Pro Lys Leu Lys Gly Lys Pro Ser Arg Glu Arg Tyr
                100                 105                 110

Val Thr His Asn Arg Ala His Trp
            115                 120
```